(12) United States Patent
Mueller et al.

(10) Patent No.: US 8,288,920 B2
(45) Date of Patent: Oct. 16, 2012

(54) ULTRASONIC TRANSDUCER FOR USE IN A FLUID MEDIUM

(75) Inventors: Roland Mueller, Steinheim (DE);
Gerhard Hueftle, Aspach (DE);
Michael Horstbrink,
Stuttgart-Feuerbach (DE); Tobias Lang,
Stuttgart (DE); Sami Radwan, Stuttgart
(DE); Bernd Kuenzl, Schwieberdingen
(DE); Roland Wanja, Markgroeningen
(DE)

(73) Assignee: Robert Bosch GmbH, Stuttgart (DE)

( * ) Notice: Subject to any disclaimer, the term of this patent is extended or adjusted under 35 U.S.C. 154(b) by 8 days.

(21) Appl. No.: 12/913,980

(22) Filed: Oct. 28, 2010

(65) Prior Publication Data
US 2011/0125024 A1 May 26, 2011

(30) Foreign Application Priority Data

Oct. 29, 2009 (DE) .......................... 10 2009 046 145

(51) Int. Cl.
*H01L 41/08* (2006.01)
(52) U.S. Cl. ........................................ 310/326; 310/327
(58) Field of Classification Search .................. 310/326, 310/327
See application file for complete search history.

(56) References Cited

U.S. PATENT DOCUMENTS

| 3,710,792 | A | * | 1/1973 | Light | 600/457 |
| 5,121,628 | A | * | 6/1992 | Merkl et al. | 73/290 V |
| 5,710,824 | A | * | 1/1998 | Mongeon | 382/162 |
| 5,737,963 | A | * | 4/1998 | Eckert et al. | 73/290 V |
| 5,920,145 | A | * | 7/1999 | Wu et al. | 310/328 |
| 6,052,879 | A | * | 4/2000 | Wu et al. | 29/25.35 |

FOREIGN PATENT DOCUMENTS

| DE | 3721209 A1 | * | 1/1989 |
| DE | 42 30 773 | | 2/1994 |
| DE | 202004002107 | * | 5/2005 |
| DE | 10 2007 010 500 | | 9/2008 |
| DE | 102007037088 A1 | * | 2/2009 |
| EP | 0 766 071 | | 4/1997 |
| WO | WO-00-79513 A1 | * | 12/2000 |
| WO | WO-00-79514 | * | 12/2000 |

* cited by examiner

*Primary Examiner* — Thomas Dougherty
(74) *Attorney, Agent, or Firm* — Kenyon & Kenyon LLP

(57) ABSTRACT

An ultrasonic transducer for use in a fluid medium includes at least one transducer core having at least one acoustic/electric transducer element. The ultrasonic transducer furthermore includes at least one decoupling element which is configured to reduce a structure-borne noise coupling between the transducer core and a housing. The decoupling element includes at least one porous plastic material, in particular a foamed plastic material. The porous plastic material includes at least one thermosetting polymer and/or at least one thermoplastic.

8 Claims, 1 Drawing Sheet

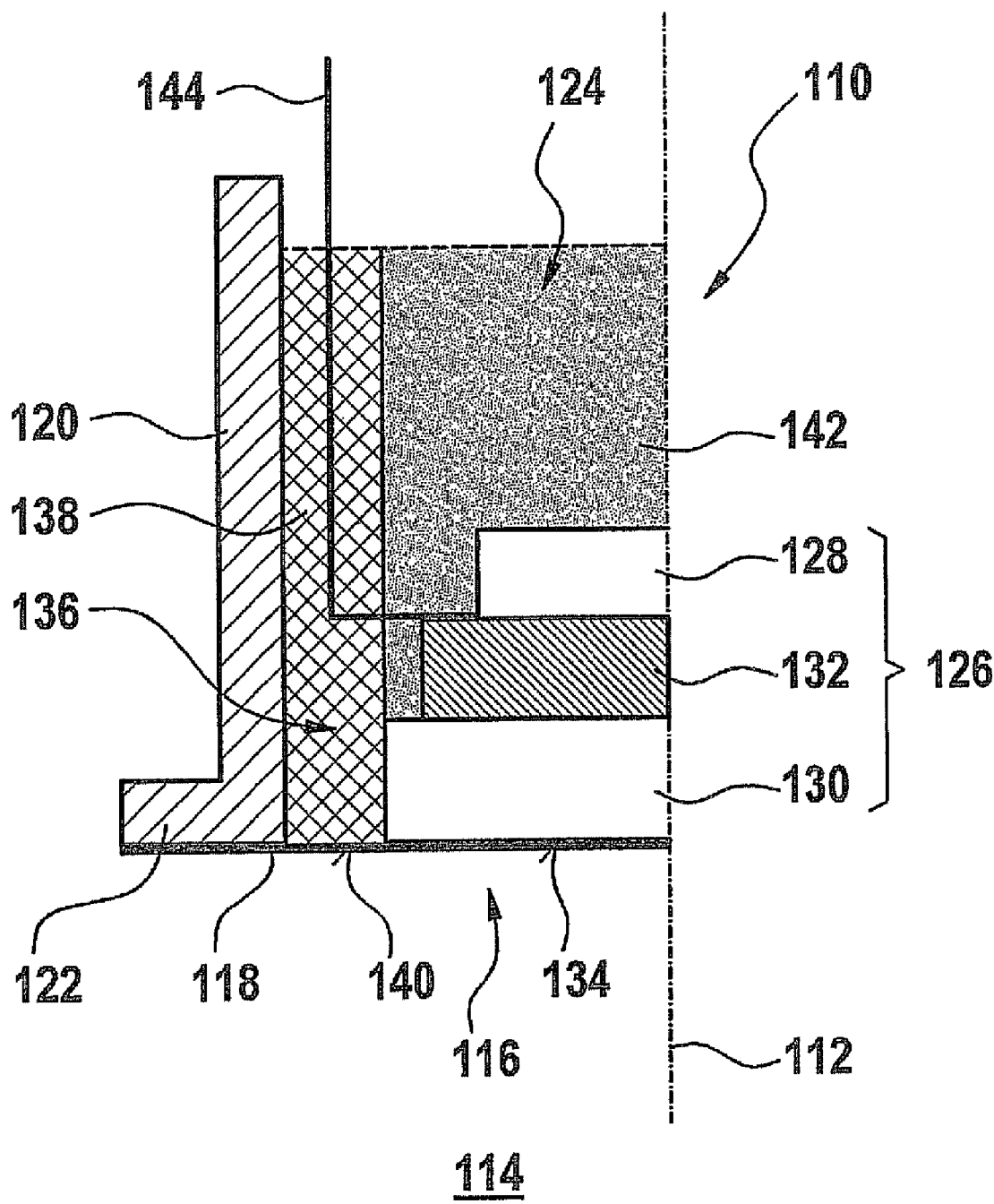

ULTRASONIC TRANSDUCER FOR USE IN A FLUID MEDIUM

CROSS-REFERENCE TO RELATED APPLICATIONS

The present application claims priority to Application No. 10 2009 046 145.0, filed in the Federal Republic of Germany on Oct. 29, 2009, which is expressly incorporated herein in its entirety by reference thereto.

FIELD OF THE INVENTION

The present application relates to an ultrasonic transducer for use in a fluid medium.

BACKGROUND INFORMATION

Certain ultrasonic transducers which may be used to radiate ultrasonic waves into a fluid medium and/or to absorb ultrasonic waves from the fluid medium are conventional. For example, ultrasonic transducers of this type may be used in ultrasonic flowmeters, for example in process engineering and/or in the automotive industry. Examples of ultrasonic transducers are described in German Published Patent Application No. 10 2007 010 500, German Published Patent Application No. 42 30 773, and European Published Patent Application No. 0 766 071.

Certain conventional ultrasonic flowmeters have air ultrasonic transducers based on a piezoceramic and which include an impedance matching layer, for example a $\lambda/4$ impedance matching layer. The impedance matching layer is used to bridge the great difference in acoustic impedances between air and ceramic. As a rule, the material of the impedance matching layer must have, on the one hand, a damping effect which is not too excessive and, on the other hand, an acoustic impedance which lies between the impedance of the fluid medium and the impedance of the piezoceramic. The theoretical optimum value for plane waves usually lies in the geometric mean of these two impedances. Due to the low air impedance, this theoretical value may usually be achieved only with the aid of extremely porous materials, such as aerogels, which, however, are less sturdy. In reality, useable results may also be obtained with the aid of high-density syntactic foams. A frequently used material for the impedance matching layer is epoxy resin filled with hollow glass spheres. Porous sintered polyimide may also be used. In many cases, a sequence of multiple layers is also used instead of a single matching layer, so that, for example, a higher ultrasonic amplitude or ultrasonic bandwidth may be achieved using step-by-step impedance matching. An additional layer may also be used to protect the piezoelectric transducer element against thermally induced tensile or shearing stresses.

Due to the impedance matching actually achieved between the piezoelectric member and the air, it is usually difficult to inject a sufficient amount of sound energy into the air or to receive it from the air in real air ultrasonic transducers, as opposed to applications in liquids. With the exception of an extremely small fraction of the actual useful signal, a large portion of the sound energy is usually reflected back to the limiting surfaces of the piezoelectric member or of the impedance matching layer. On the other hand, the injection of the structure-borne noise from the piezoelectric member into its attachment, for example via a damping casting, a decoupling element, a transducer housing, or the like, is usually counteracted by only comparatively small impedance differences. Even if a transducer core is embedded into a soft silicone, a parasitic sound transfer to the surrounding materials and/or to a second transducer usually still occurs, which is implemented in many cases, for example, to measure flow. This parasitic sound transfer is usually much stronger that the actual useful signal through the air, and it also usually does not sufficiently subside until the actual useful signal arrives. Accordingly, a structure-borne noise decoupling is used in many cases by implementing silicone- and/or elastomer-molded parts, such as O rings. Decoupling is usually improved by geometric shaping, for example by reducing the geometry to a merely linear coupling of an O ring to the transducer core, if necessary also in vibration nodes of the transducer housing.

An ultrasonic transducer for use in a fluid medium is described in German Published Patent Application No. 10 2008 055 126. In this ultrasonic transducer, it is described, among other things, to provide a decoupling element between a housing of the ultrasonic transducer and a matching body. Elastomer materials, which may include gas-filled hollow spheres or gas inclusions, are proposed as examples of materials of decoupling elements of this type.

A disadvantage of these approaches, however, is a usually insufficient media resistance of the decoupling materials used or of the connecting points between the decoupling material and the adjacent materials. This disadvantage may usually be overcome by a suitable coating, for example a Teflon coating, a parylene layer, or a lacquer layer. In principle, a film may also be used for sealing, for example in connection with an open-pore matching layer, made for example of porous sintered polyimide. If the ultrasonic transducer is also to withstand pressure loads, the coating and/or the film should, however, be in direct and continuous contact with the impedance matching layer, the decoupling material and the further transducer environment, for example a sleeve or a housing, to be able to withstand corresponding forces. This is extremely difficult, in light of assembly tolerances of the relatively soft decoupling molded parts.

SUMMARY

According to example embodiments of the present invention, an ultrasonic transducer for use in a fluid medium and a method for manufacturing an ultrasonic transducer for use in a fluid medium are provided, which at least partially avoid the disadvantages of conventional ultrasonic transducers. The ultrasonic transducer may be manufactured, in particular, according to a manufacturing method described herein, and the manufacturing method may be used to manufacture an ultrasonic transducer as described herein so that reference may be made to the description of the ultrasonic transducer with regard to possible arrangements of the method and vice-versa.

An ultrasonic transducer for use in a fluid medium is provided, for example, in which the ultrasonic transducer may be used, as described above, in a gaseous medium (for example air and/or exhaust gas) or in another type of fluid medium. In particular, the ultrasonic transducer may be used for a flow measurement, for example in flowmeters for the automotive industry. The ultrasonic transducer includes at least one transducer core, the transducer core including at least one acoustic/electric transducer element. In principle, an acoustic/electric transducer element should be understood to be any transducer element which is able to convert electric signals to acoustic signals, in particular ultrasonic signals, and/or vice-versa. For example, the acoustic/electric transducer element may include at least one piezoelectric transducer member. Furthermore, the transducer core may include at least one matching body for improving the coupling properties between the fluid medium and the acoustic/electric transducer element, as discussed in greater detail below, for example a λ/4 impedance matching layer or multiple layers of this type. Alternatively or in addition, the transducer core may include additional elements, as discussed in greater detail below, for example one or more thermal matching layers which may be situated alone or also, for example, between the acoustic/electric transducer element and a matching body. Furthermore, the transducer core may preferably have a radiation surface facing the fluid medium for decoupling and/or injecting ultrasonic waves. This radiation surface preferably remains at least partially uncovered by the decoupling element, which is explained in greater detail below.

The ultrasonic transducer furthermore includes at least one decoupling element. The decoupling element is configured to at least reduce a structure-borne noise coupling between the transducer core and a housing. For this purpose, the decoupling element has at least one porous plastic material. In principle, a porous plastic material should be understood to be any plastic material which has a plurality of cavities which may have a contiguous or non-contiguous design. In principle, the cavities may be produced in a variety of manners. The cavities are particularly preferably embedded directly into a matrix of the plastic material, for example non-encapsulated in the form of hollow spheres. In this case, the cavities are provided directly as cavities in the matrix, for example in a matrix material of the matrix, for example in the form of pores. However, an encapsulation is also possible in principle. For example, hollow bodies may be embedded into the matrix. Rigid hollow glass bodies, for example hollow glass spheres, are usable in principle, although they are less preferred. Alternatively or in addition, hollow plastic bodies are advantageously usable, for example hollow plastic spheres which preferably have a certain compressibility. Again as an alternative or in addition, cavities not having any sheathing are also usable, as discussed above. The pores of the porous plastic material may be filled, for example by a gas or also by vacuum. Examples are specified in greater detail below. In particular, the porous plastic material may have a foamed plastic material. The porous plastic material includes at least one thermosetting polymer and/or at least one thermoplastic. In particular, the at least one thermosetting polymer and/or the at least one thermoplastic may be used as a matrix material, preferably as a homogeneous matrix material, into which the pores or cavities, for example the hollow bodies, are directly embedded. A thermoplastic or plastomer is a plastic which is largely not deformable or is only insignificantly deformable at least within the application temperature range of the ultrasonic transducer, for example, within a temperature range of −40° C. to +110° C., while heating within a higher temperature range, such as above a glass transition temperature, results in deformability. A thermosetting polymer or duromer is generally understood to be a plastic which is no longer deformable or is only insignificantly deformable after it is cured. For further possible delimitations between thermoplastic/thermosetting materials and other plastic materials, such as elastomers, reference may be made, for example, to Hans-Georg Elias, Macromolecules, Vol. 3: Physical Structures and Properties, 2008, page 2.

The plastic material may include, in particular, one or more of the following plastic materials: a porous thermoplastic material; a foamed thermoplastic material; a porous thermosetting material; a foamed thermosetting material a porous epoxy resin; a foamed epoxy resin. Foamed epoxy resins, in particular, are considered suitable with regard to their processing properties as well as with regard to their suitability as decoupling elements. The decoupling elements may be introduced into the ultrasonic transducer as finished molded parts, or as an alternative or in addition, the decoupling element may be molded entirely or partially within the ultrasonic transducer, for example within the housing of the ultrasonic transducer, for example in a gap between the transducer core and the housing of the ultrasonic transducer. Different exemplary embodiments are described in greater detail below.

The porous plastic material may have, in particular, a degree of porosity of at least 5 vol % and preferably at least 10 vol %. The porous plastic material may preferably have cavities having an average diameter of 5 μm to 200 μm, in particular less than 80 μm, for example between 5 μm and 50 μm. In principle, however, other ranges are also possible.

The ultrasonic transducer may furthermore include at least one housing. This housing may at least partially surround the transducer core. A gap, for example an annular gap, may be provided between the housing and the transducer core. This gap may be at least partially filled by the decoupling element. This gap is preferably filled such that the radiation surface of the transducer core described above remains at least partially free of the decoupling material. For example, the gap may be arranged such that, viewed from the direction of the fluid medium, the radiation surface of the transducer core is surrounded in an annular manner by a surface of the decoupling element, which, in turn, is surrounded in an annular manner by the housing. A round, in particular circular, geometry, a polygonal geometry or, in principle, any geometry of the annular shape may be provided. In the illustrated exemplary embodiment, the radiation surface of the transducer core, the limiting surface of the decoupling element and the edge of the housing, which face the fluid medium, preferably form a substantially flat surface.

According to example embodiments of the present invention, a method for manufacturing an ultrasonic transducer for use in a fluid medium is provided, in particular an ultrasonic transducer in one or more of the example embodiments illustrated above. At least one transducer core is provided, which includes at least one acoustic/electric transducer element. Furthermore, at least one decoupling element is provided, which is configured to at least reduce a structure-borne noise coupling between the transducer core and a housing, for example a housing of the ultrasonic transducer itself or a further housing into which the ultrasonic transducer is embedded. At least one porous plastic material, in particular a foamed plastic material, is used to manufacture the decoupling element, the porous plastic material including at least one thermosetting polymer and/or at least one thermoplastic.

In particular, at least one basic material in which gas bubbles are produced by chemical foaming and/or physical foaming and/or mechanical foaming may be provided for manufacturing the decoupling element. Chemical foaming is generally understood to be foaming in which the formation of foam is induced by a chemical reaction. Physical foaming is understood to be foaming in which phase transitions, for example selective phase transitions from a liquid to a gaseous state, are utilized to produce gas bubbles. Mechanical foaming should generally be understood to be a method in which one or more gases is/are added directly to the basic material, thereby causing the basic material to foam. In addition to these cavities produced by one or more of the aforementioned types of foaming, additional types of cavities may be optionally present in the decoupling element in each case, for example in the form of the hollow plastic bodies described above.

For example, a basic material may be provided by producing gas bubbles with the aid of at least one chemical reaction.

For example, two-component mixtures may be used which together perform a chemical reaction in which gases are released. A mixture of more than two components is also possible. For example, epoxy resin mixtures which are used to manufacture epoxy foams are mixtures of this type having at least two components. Exemplary embodiments are specified in greater detail below.

In principle, a basic material is understood to be any material which forms the decoupling element, either alone or in combination with other materials. For example, this may be one or more precursors of the decoupling element from which the porous plastic material having the at least one thermosetting polymer and/or the at least one thermoplastic is formed.

A physical foaming method may be used as an alternative or in addition to the chemical-foaming methods described. For example, the basic material may include at least one foaming component. The basic material is expanded, forming the foaming components of gas bubbles. In particular, the foaming component may include a gas in a supercritical state. During expansion, this gas, which in its supercritical state is present in the liquid state, changes back to its gaseous state, in which it is present under normal conditions. In particular, one or more of the following gases may be used: ambient air; nitrogen, carbon dioxide; argon. As described above, a mechanical-foaming method may be furthermore used as an alternative or in addition, for example, also using one or more of the aforementioned gases.

Chemical foaming may be carried out entirely or partially during and/or after introduction of the decoupling element into the ultrasonic transducer. For example, the chemical and/or physical and/or mechanical foaming may be carried our during and/or after injection of the at least one basic material into a gap between the transducer core and the housing. However, a previously foamed decoupling element may also be introduced as an alternative or in addition, it being possible, for example, to carry out the foaming and/or molding operations separately, so that the molded part which is introduced is already premolded and prefoamed. Different arrangements are possible.

As mentioned above, a further possibility for manufacturing the decoupling element exists as an alternative or in addition to the described foaming methods in the use of hollow bodies, which may provide the porosity of the plastic material or at least a portion of this porosity. For example, at least one basic material may again be provided for manufacturing the decoupling element, for example in the manner described above. For example, this may be the same basic material or, if one or more of the foaming methods is used, a different type of basic material from which the porous plastic material is later produced. Hollow bodies, in particular hollow plastic bodies, may be mixed into this basic material as described above. For example, flexible hollow bodies may be used. In particular, hollow plastic spheres may be used. The hollow bodies may have, for example, cavities having an average equivalent diameter of 1 micrometer to 200 micrometers, preferably 5 micrometers to 80 micrometers, and particularly preferably 10 micrometers to 80 micrometers. These dimensions are generally also preferred for cavities in the decoupling element which are produced in a different manner.

The ultrasonic transducer and the method described herein are considered to have numerous advantages over conventional ultrasonic transducers and methods. In particular, parasitic ultrasound paths within the materials of the ultrasonic transducers and/or the housing, in particular a sensor housing, may be substantially reduced, in particular structure-borne noise, which would otherwise corrupt the measuring signal. This makes it possible to prevent the ascertained value for the flow rate to be measured from exceeding the required tolerance limits. At the same time, example embodiments of the present invention provide dimensionally stable suspension of the transducer core. A stress-free and thus permanently media-tight sealing layer may simultaneously be implemented.

For example, a casting and/or injection process may be used to manufacture the ultrasonic transducer, in particular the decoupling element. Despite the fact that the connection to the transducer core in this case tends to be over a wide area instead of at specific points or in a linear manner, the decoupling may be implemented by the material properties of the decoupling element. In this manner, a suitable damping may be achieved, for example by scattering at the pores of the porous plastic material, for example by an impedance mismatch between the transducer core and the housing. A mismatch of this type may be further supported by selecting largely effective layer thicknesses of the decoupling element along the directions of structure-borne noise propagation such that multiple reflections on the corresponding limiting surfaces which limit the decoupling element interfere with each other in a largely destructive manner. In contrast to silicones, the described porous thermosetting polymers and/or thermoplastics have a relatively high modulus of elasticity, on the one hand, and a high material-intrinsic damping, on the other hand. For example, an adiabatic compression in the cavities may result in improved damping.

Furthermore, decoupling with the aid of the porous plastic materials having porous thermoplastics and/or thermosetting polymers may be used to overcome the disadvantage of an elastic decoupling described above. This makes it possible, for example, to provide a front surface of the ultrasonic transducer with a largely dimensionally stable design even under thermal loads and/or pressure loads. For example, this front surface may include an edge of the housing, for example a sleeve edge, as well as an end face of the decoupling element and a radiation surface of the transducer core. As described above, this front face may be preferably provided with a largely flat design. An additional sealing element, for example a sealing coating and/or a sealing film, may be optionally applied to the front surface. For example, a sealing coating made of parylene may be used. The sealing film may include, in particular, a plastic film. For example, plastic films having a thickness of less than 100 micrometers, in particular less than 50 micrometers, particularly preferably 25 micrometers or less may be used. The sealing element may include a thermoplastic material or a thermosetting material, in particular one or more of the following materials: a polyimide, in particular Kapton®; a fluorinated polymer, in particular polytetrafluoroethylene (PTFE), Teflon®; a polyvinyl fluoride (PVF); a polyether ether ketone (PEEK); a polymethyl methacrylate (PMMA); a polyamide imide (PAI); a liquid crystal polymer (LCP); a polyether sulfone (PES); a polysulfone (PSU); a polyethylene naphthalate (PEN); a polyphenylene sulfide (PPS); a fluorinated ethylene propylene (FEP); a metallic, plastic-like or ceramic coating; an adhesive layer. Combinations of the aforementioned materials and/or other materials are possible. As an alternative or in addition, other materials, other layer thicknesses or also laminates may be used.

The attachment of these sealing elements and/or the sealing element itself is then subjected to much less stress than is the case in conventional ultrasonic transducers under the aforementioned conditions, due to the use of the preferably largely dimensionally stable decoupling element.

Exemplary embodiments of the present invention are illustrated in the drawing and explained in greater detail in the following description.

BRIEF DESCRIPTION OF THE DRAWING

FIG. 1 shows an sectional representation of an exemplary embodiment of an ultrasonic transducer.

DETAILED DESCRIPTION

FIG. 1 shows a sectional representation of an exemplary embodiment of an ultrasonic transducer 110, viewed from the side. In the illustrated exemplary embodiment, ultrasonic transducer 110 is arranged by way of example to be rotationally symmetrical around an axis of symmetry 112, other arrangement also being possible, however. Ultrasonic transducer 110 is provided for use in a fluid medium, for example air, which is identified symbolically by reference numeral 114 in FIG. 1. A front surface 116 of ultrasonic transducer 110 faces fluid medium 114. This front surface 116 may be sealed, for example, by a sealing film 118.

Ultrasonic transducer 110 includes a housing 120, which may be arranged, for example, as a sleeve. The housing is open toward fluid medium 114 or toward front surface 116 and has an edge 122 facing fluid medium 114. Sealing film 118 may be connected to this edge 122 in an integral manner and/or another manner, for example by gluing.

A transducer core 126 is accommodated in an interior 124 of housing 120. This transducer core 126 includes at least one acoustic/electric transducer element 128. In the illustrated exemplary embodiment, transducer core 126 furthermore includes an optional matching body 130 for improving injection of ultrasonic waves of acoustic/electric transducer element 128 into the fluid medium and/or for improving decoupling of ultrasonic waves out of fluid medium 114. Matching body 130 may be arranged, for example, according to the matching bodies described in the documents mentioned above. In particular, matching body 130 may include one or more λ/4 matching layers.

Furthermore, at least one compensating element 132 may be optionally accommodated in transducer core 126, for example to reduce thermomechanical stresses. Examples of a compensating element 132 of this type are explained in greater detail below. Without limiting further possible arrangements of acoustic/electric transducer element 128, the latter is also generally referred to below simply as piezoelectric member or piezoceramic. Without limiting further possible arrangements of the matching body, this element is also referred to below as a matching layer, and compensating element 132 is also referred to as CTE matching element or CTE compensating layer (CTE: coefficient of thermal expansion). Compensating element 132 may be arranged as a single layer between acoustic/electric transducer element 128 and matching body 130. However, it may also optionally have a more complex geometry.

Transducer core 126 has a radiation surface 134 which faces fluid medium 114. This radiation surface 134 preferably remains largely uncovered and, as illustrated in FIG. 1, it may be entirely or partially covered by sealing film 118 and/or another sealing element, for example a coating. Radiation surface 134 is preferably situated on the same plane as edge 122 of housing 120.

In the illustrated exemplary embodiment, a gap 136 is provided between transducer core 126 and housing 120. This gap 136 has, for example, an annular design. Gap 136 is filled by a decoupling element 138, which includes a porous plastic material having at least one thermosetting polymer and/or at least one thermoplastic. Exemplary embodiments are explained in greater detail below. In the illustrated exemplary embodiment, decoupling element 138 preferably has an end face 140 which faces fluid medium 114 and which preferably has a flat design and which is preferably situated on the same plane as edge 122 and/or radiation surface 134. In the illustrated exemplary embodiment, end face 140, radiation surface 134 and edge 122 may be optionally sealed by sealing film 118, as discussed above.

In the illustrated exemplary embodiment, ultrasonic transducer 110 furthermore has a damping casting 142, which is mounted, for example, on the back or on transducer core 126. This damping casting 142, which may be attached by any other method as an alternative or in addition to the casting method, should accelerate the decay behavior of acoustic/electric transducer element 128. For example, it may be a silicone casting or another type of soft material, which may completely or partially fill remaining gap 136, for example.

A electric supply line 144 for acoustic/electric transducer element 128 is furthermore illustrated symbolically in FIG. 1. As a rule, acoustic/electric transducer element 128 includes one, two or more such electric supply lines 144. The routing of this electric supply line 144 is shown only by way of example, and the supply line is routed in this case, for example, through compensating element 132 and decoupling element 138. As an alternative or in addition, this electric supply line 144 may, however, also be routed completely or partially through damping casting 142, for example. Different embodiments are possible.

In ultrasonic transducer 110 according to FIG. 1, acoustic/electric transducer element 128 is connected to impedance matching layer 130, for example via compensating element 132. In the simplest case, this connection may be, for example, an adhesive layer which is hard enough and has a high modulus of elasticity (E modulus) to achieve a sufficient acoustic coupling. In particular, epoxy adhesives may be used for this purpose.

Since piezoceramics react sensitively to tensile and shearing stresses, which may arise for example due to the thermal expansion of matching layer 130, flexibilized epoxy adhesives may, in principle, also be used, it being necessary for parameters such as the glass transition point (Tg) to be high enough for a sufficient acoustic coupling to be achieved throughout the entire required temperature range. For example, ultrasonic transducer 110 may be used within a temperature range between −40° C. and 110° C. or even, at least with limited functionality, at temperatures up to 140° C. Accordingly, the material of compensating element 132 may have a Tg of, for example, over 150° C. A selection of materials having a glass transition temperature of over 150° C. is advantageous for other materials as well, for example for decoupling element 138.

The material of matching layer 130 may also be connected directly to acoustic/electric transducer element 128, for example by first connecting the piezoelectric member of acoustic/electric transducer element 128 to an as yet uncured material of matching body 130 and subsequently curing, for example cross-linking, the piezoelectric member.

However, if a separate adhesive layer is used for compensating element 132, this layer may be relatively thick. In this case, flexibility of this material may be intentionally dispensed with, for example, and instead a coefficient of thermal expansion (CTE) between the coefficient of thermal expansion of the piezoelectric member of acoustic/electric transducer element 128 and that of matching body 130 may be set, or ideally this coefficient of thermal expansion may be set to a value as close as possible to that of the piezoelectric member. Warping may then be reduced via the thickness of this CTE compensating layer.

The piezoelectric member, the CTE compensating layer and matching layer 130 may be glued together as separate parts, or alternatively the CTE compensating layer and/or matching layer 130 may also be brought into contact with each other or with the piezoelectric member without using a separate adhesive and subsequently cured. A film may be used as a lost mold for the decoupling material of decoupling element 138 and then optionally remain on ultrasonic transducer 110 as a sealing layer, as an alternative or in addition to sealing film 118.

The functions of impedance matching and compensation of the coefficients of thermal expansion may also be implemented within a single component. In this or in other exemplary embodiments, for example, matching body 130 and compensating element 132 may be completely or partially combined. In this manner, a single part may be used, for example, which may be arranged accordingly with regard to CTE and/or flexibility and/or acoustic impedance, it being possible to also abruptly or gradually change the corresponding material properties between the piezoceramic and radiation area. For example, fillers such as hollow glass spheres and/or ceramic particles may be mixed into an epoxy basic material. For the purpose of reducing density, hollow glass spheres may be used to match the impedance and may therefore tend to float in the direction of the radiation area, while ceramic particles may be deposited in the direction of piezoelectric member 128 as a CTE matching function. The desired material properties may be achieved in this manner.

To place acoustic/electric transducer element 128 in the neutral state as quickly as possible after transmission, the acoustic/electric transducer element in the illustrated exemplary embodiment is in contact with damping casting 142, which may include, in principle, any damping material (such as silicone or filled silicone). For example, if a planar resonance of a piezoelectric member is primarily utilized, it is also advantageously connected to the material of damping casting 142 partially or completely along its circumference to enable as much sound energy as possible to be decoupled into the damping component. An even better damping may be achieved if compensating element 132 is also in contact with the material of damping casting 142.

Alternatively, however, another method may be used to introduce decoupling element 138, for example a casting method and/or an injection method. For example, a stamping tool may be used, in which a stamp is inserted into interior 124 of housing 120 from the rear, for example after introducing transducer core 126. This stamping tool may be used to keep the space free for damping casting 142 and/or for parts of transducer core 126 or for entire transducer core 126 while the material of decoupling element 138 is being introduced.

As illustrated above, a porous plastic material having at least one thermosetting polymer and/or at least one thermoplastic is used for decoupling element 138. As discussed above, a porous material is understood to be, in principle, any material having pores or cavities. Examples of porous materials of this type include foamed materials, in particular porous or foamed thermoplastic or thermosetting materials.

Multiple alternative methods may be used to produce materials of this type, for example for manufacturing decoupling element 138 in situ and/or as a premolded part. In an exemplary embodiment of manufacturing decoupling element 138, basic materials in which a chemical reaction produces gas bubbles may be used as basic components. Examples of basic materials of this type include the epoxy systems having the designation PB 170, PB 250, PB 400 or PB 600 from the company Composite Solutions AG in 3018 Bern, Switzerland. Materials of this type are customarily used as foams for building boats and/or aircraft. Unlike in these typical primary areas of application, the basic components, mixing conditions, and curing temperature profiles in the present case are preferably selected such that the highest possible glass transition point results. In general, thermosetting materials are thus preferably foamed by a chemical-foaming method. However, physical and/or mechanical methods are, in principle, also possible as an alternative or in addition. Thermoplastic materials, on the other hand, are preferably foamed by a physical foaming method, it being also possible, however, to use other alternative foaming methods, such as mechanical-foaming methods. In addition, an admixture of hollow bodies may optionally be carried out, for example an admixture of flexible hollow plastic bodies, in particular hollow plastic spheres.

As a further example for manufacturing a foamed plastic material, porous thermoplastics may be used which may be manufactured, for example, according to the so-called MuCell method. In this method, a gas, for example from the ambient air, for example nitrogen or carbon dioxide, is brought into a supercritical state. This gas in the supercritical state (which is then naturally no longer gaseous, but which is present in a gaseous state only under normal conditions) may then be used as the foaming agent. The supercritical fluid may be metered as precisely as a conventional liquid, and it may be distributed uniformly and dissolved, for example, in a plastic melt. Due to the pressure drop during injection into a mold, tiny gas bubbles then arise, which continue to grow during the cooling phase and thus compensate for the shrinkage of the part. This results in extremely fine-cell foam cells having diameters primarily between 5 µm and 50 µm, it being possible to typically set the degree of porosity up to 30% or even up to 40% or higher. Decoupling materials manufactured in this manner are dimensionally relatively stable and non-compressible compared, for example, to silicones. In contrast to matching body 130, the cavities in the decoupling element are thus preferably not formed by hollow glass spheres, but rather by chemical or physical foaming. This makes it possible to generate a largely ultrasonic damping and scatter, as opposed to matching body 130, within which this effect is downright undesirable.

In principle, other methods may also be used as an alternative or in addition. Pressing and/or sintering methods may be used as further alternatives or additional examples for manufacturing a foamed plastic material.

As an alternative to foaming and curing the material of decoupling element 130 directly in ultrasonic transducer 110 or its housing 120 or at or in a construction stage of ultrasonic transducer 110, decoupling element 138 may also be prefabricated as a separate component and then mounted together with other individual parts and/or assemblies of ultrasonic transducer 110, for example by gluing. In the case of pressure loads from the outside and/or in the case of thermal expansion or contraction within ultrasonic transducer 110, for example within transducer core 126, preferably dimensionally stable decoupling element 138 enables force to be transferred at little mobility and thus stabilizes the position of transducer core 126. At the same time this also makes it possible to attach an expansion sensitive- or shear sensitive-sealing film 118 and/or a coating to front surface 116. The material of decoupling element 138 thus preferably acts in a similar manner to a low pass filter, which transfers low frequencies due to its dimensional stability under static or relatively slowly varying loads, and blocks higher frequencies, which results in an ultrasonic decoupling or ultrasonic damping.

In the exemplary embodiment according to FIG. 1, housing 120 of ultrasonic transducer 110, which may be designed, for example, entirely or partially as a sleeve, represents only one possible arrangement. Thus, this housing 120 may also simultaneously be a subarea of a larger sensor housing, which may also accommodate, for example, other components, such as control electronics and/or measurement electronics and/or evaluation electronics and/or a second ultrasonic transducer 110. Multiple ultrasonic transducers 110 may therefore also share a common housing 120 or at least common housing components of this housing 120.

In principle, sealing film 118 may be manufactured from any material. In particular, the use of metals and/or plastics is preferred. For example, one or more of the following materials may be used: a polyimide, in particular Kapton®; a polyether ether ketone (PEEK); a polyvinyl fluoride (PVF), in particular Tedlar®; a polytetrafluoroethylene (PTFE), in particular Teflon®. Other materials, in particular other polymers, may be used as an alternative or in addition. The thickness of sealing film 118 should preferably not greatly exceed 100 μm, on the one hand, to avoid excessively hindering injection of ultrasound into fluid medium 114, for example air, and, on the other hand, to avoid excessively increasing the transmission of structure-borne noise past the material of decoupling element 138 via sealing film 118. Thicknesses of 25 μm or less are particularly advantageous. As an alternative or in addition to a sealing element in the form of a sealing film 118, other types of sealing elements may be used, for example a coating. Parylene, Teflon, epoxy lacquers or similar materials are examples of coatings of this type. Such coatings may be manufactured, for example, such that they form a contiguous layer only after being applied to front surface 116.

What is claimed is:

1. An ultrasonic transducer for use in a fluid medium, comprising:
at least one transducer core, the transducer core including at least one acoustic/electric transducer, the ultrasonic transducer including at least one decoupling device, the decoupling device configured to reduce a structure-borne noise coupling between the transducer core and a housing, the decoupling device including at least one porous plastic material, the porous plastic material including at least one of (a) at least one thermosetting polymer and (b) at least one thermoplastic.

2. The ultrasonic transducer according to claim 1, wherein the porous plastic material includes a foamed plastic material.

3. The ultrasonic transducer according to claim 1, wherein the plastic material includes at least one of the following plastic materials: (a) a porous thermoplastic material; (b) a foamed thermoplastic material; (c) a porous thermosetting material; (d) a foamed thermosetting material; (e) a porous epoxy resin; and (f) a foamed epoxy resin.

4. The ultrasonic transducer according to claim 1, wherein the porous plastic material has a degree of porosity of at least one of (a) at least 5 percent by volume and (b) at least 10 percent by volume.

5. The ultrasonic transducer according to claim 1, wherein the porous plastic material has cavities having an average diameter of 5 to 200 micrometers.

6. The ultrasonic transducer according to claim 1, further comprising a housing at least partially surrounding the transducer core, at least one gap arranged between the housing and the transducer core, the gap at least partially filled by the decoupling element.

7. The ultrasonic transducer according to claim 6, wherein the gap includes an annular gap.

8. A method for manufacturing an ultrasonic transducer for use in a fluid medium according to claim 1, comprising:
providing at least one transducer core including at least one acoustic/electric transducer;
providing at least one decoupling device configured to reduce a structure-borne noise coupling between the transducer core and a housing, at least one porous plastic material being used to manufacture the decoupling element, the porous plastic material including at least one of (a) at least one thermosetting polymer and (b) at least one thermoplastic.

* * * * *